(12) United States Patent
Chishti

(10) Patent No.: US 6,783,360 B2
(45) Date of Patent: Aug. 31, 2004

(54) SYSTEMS AND METHODS FOR POSITIONING TEETH

(75) Inventor: Zia Chishti, Sunnyvale, CA (US)

(73) Assignee: Align Technology, Inc., Santa Clara, CA (US)

(*) Notice: Subject to any disclaimer, the term of this patent is extended or adjusted under 35 U.S.C. 154(b) by 27 days.

(21) Appl. No.: 09/737,313

(22) Filed: Dec. 13, 2000

(65) Prior Publication Data

US 2002/0072027 A1 Jun. 13, 2002

(51) Int. Cl.$^7$ .................................................. A61C 3/00
(52) U.S. Cl. ......................................................... 433/6
(58) Field of Search ................................ 433/6, 18, 20, 433/24, 215

(56) References Cited

U.S. PATENT DOCUMENTS

| | | |
|---|---|---|
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,860,803 A | 1/1975 | Levine |
| 3,922,786 A | 12/1975 | Lavin |
| 3,950,851 A | 4/1976 | Bergersen |
| 4,253,828 A | 3/1981 | Coles et al. |
| 4,324,546 A | 4/1982 | Heitlinger et al. |
| 4,324,547 A | 4/1982 | Arcan et al. |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,591,341 A | 5/1986 | Andrews |
| 4,609,349 A | 9/1986 | Cain |
| 4,664,626 A | 5/1987 | Kesling |
| 4,676,747 A | 6/1987 | Kesling |
| 4,755,139 A | 7/1988 | Abbatte et al. |

(List continued on next page.)

FOREIGN PATENT DOCUMENTS

| | | |
|---|---|---|
| FR | 2369828 | 6/1978 |
| WO | WO 94/10935 | 5/1994 |
| WO | WO 98/32394 | 7/1998 |
| WO | WO 98/58596 | 7/1998 |

OTHER PUBLICATIONS

Andrews, "The Six Keys to Optimal Occlusion" *Straight Wire*, Chapter 3 pp 13–24.

Biostar Opeation & Training Manual. Great Lakes Orthodontics, Ltd. 199 Fire Tower Drive, Tonawanda, New York. 14150–5890. 20 pages total.

Chiappone, "Constructing the gnathologic setup and positioner" *J. Clin. Orthod.* (1980) 14:121–133.

Cottingham, "Gnathologic clear plastic positioner" *Am. J. Orthod.* (1969) 55:23–31.

Cureton, "Correcting malaligned mandibular incisors with removable retainers" *J. Clin. Orthod.* (1996) 30:390–395.

Dent–X posted at http://www.dent–x.com/DentSim.htm Sep. 24, 1998, 6 pages ttoal.

(List continued on next page.)

*Primary Examiner*—Ralph A. Lewis
(74) *Attorney, Agent, or Firm*—Townsend and Townsend and Crew LLP; Bao Tran, Esq.

(57) ABSTRACT

A computer-implemented method treats teeth by generating a digital arrangement of teeth; specifying a sequence of tooth movements to move the teeth to a target arrangement; and generating one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

18 Claims, 13 Drawing Sheets

U.S. PATENT DOCUMENTS

| | | |
|---|---|---|
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,936,862 A | 6/1990 | Walker et al. |
| 4,941,826 A | 7/1990 | Loran et al. |
| 4,983,334 A | 1/1991 | Adell |
| 5,011,405 A | 4/1991 | Lemchen |
| 5,017,133 A | 5/1991 | Miura |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,125,832 A | 6/1992 | Kesling |
| 5,139,419 A | 8/1992 | Andreiko et al. |
| 5,145,364 A | 9/1992 | Martz et al. |
| 5,186,623 A | 2/1993 | Breads et al. |
| 5,273,429 A | 12/1993 | Rekow et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Anderson et al. |
| 5,605,459 A | 2/1997 | Kuroda et al. |
| 5,607,305 A | 3/1997 | Andersson et al. |
| 5,645,420 A | 7/1997 | Bergersen |
| 5,645,421 A | 7/1997 | Slootsky |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,800,174 A | 9/1998 | Andersson |
| 5,866,058 A | 2/1999 | Batchelder et al. |
| 5,879,158 A | 3/1999 | Doyle et al. |
| 5,880,961 A | 3/1999 | Crump |
| 5,957,686 A | 9/1999 | Anthony |
| 5,964,587 A | 10/1999 | Sato |
| 5,971,754 A | 10/1999 | Sondhi et al. |
| 5,975,893 A * | 11/1999 | Chishti et al. ............... 433/6 |
| 6,044,309 A | 3/2000 | Honda |
| 6,049,743 A | 4/2000 | Baba |
| 6,123,544 A | 9/2000 | Cleary |
| 6,183,248 B1 | 2/2001 | Chishti et al. |
| 6,190,165 B1 | 2/2001 | Andreiko et al. |
| 6,217,334 B1 | 4/2001 | Hultgren |
| 6,406,292 B1 * | 6/2002 | Chishti et al. ............... 433/24 |

OTHER PUBLICATIONS

Elsasser, "Some observations on the history and uses of the Kesling positioner" *Am. J. Orthod.* (1950) 36:368–374.

Kamada et al., "Case reports on tooth positioners using LTV vinyl silicone rubber" *J. Nihon University School of Dentistry* (1984) 26(1):11–29.

Kamada et al., "Construction of tooth positioners with LTV vinyl silicone rubber and some case reports" *J. Nihon University School of Dentistry* (1982) 24(1):1–27.

Kesling, "Coordinating the predetermined pattern and tooth positioner with conventional treatment" *Am. J . Orthod. Oral. Surg.* (1946) 32:285–293.

Kesling, "The philosophy of the tooth positioning appliance" *Am. J. Orthod. Oral. Surg.* (1945) 31(6):297–304.

Kleeman et al., "The speed positioner" *J. Clin. Orthod.* (1996) 30:673–680.

Kunii et al., "Articulation Simulation for an Intelligent Dental Care System" *Displays* (1994) 15:181–188.

Kuroda et al., "Three–dimensional dental cast analyzing system using laser scanning" *Am. J. Orthod. Dentofac. Orthop.* (1996) 110:365–369.

Nahoum et al., "The vacuum formed dental contour appliance" *The New York State Dental Journal* (1964) 30(9):385–390.

*Nippon Dental Review* "New orthodontic device–dynamic positioner (D.P.)–I. Approach to the proposal of D.P. and transparent silicone rubber" (1980) 452:61–74.

*Nippon Dental Review* "New orthodontic device–dynamic positioner (D.P.)–II. Practical application and construction of D.P." (1980) 454:107–130.

*Nippon Dental Review* "New orthodontic device–dynamic positioner (D.P.)–III. Case reports of reversed occlusion" 1980) 457:146–164.

*Nippon Dental Review* "New orthodontic device–dynamic positioner (D.P.)–Case reports of reversed occlusion"to (1980) 458:112–129.

Nishiyama et al., "A new construction of tooth repositioner by LTV vinyl silicone rubber" *J. Nihon University School of Dentistry* (1977) 19(2):93–102.

Cardinal Industrial Finishes, Powder Coatings information posted at http://www.cardinalpaint.com on Aug. 25, 2000, 2 pages total.

Proffit et al, "Contemporary Orthodontics" Second Edition, Chapter 15, pp 470–533.

*Raintree Essix™ & ARS Materials, Inc.*, Raintree Essix™ Technical Magazine Table of Contents and Essix™ Applications, http://www.essix.com/magazine/default.html (Aug. 13, 1997) 7 pages total.

Richmond et al., "The development of the PAR Index (Peer Assessment Rating): reliability and validity" *European Journal of Orthodontics* (1992) 14:125–139.

Schroeder et al., Eds. *The Visual Toolkit*, Prentice Hall PTR, New Jersey (1998) Chapters 6, 8, and 9 (pp. 153–210, 309–354, and 355–428, respectively).

Shilliday, "Minimizing finishing problems with the mini–positioner" *Am. J. Orthod.* (1971) 59:596–599.

Warunek et al., "Clinical use of silicone elastomer applicances" *JCO* (1989) XXIII(10):694–700.

Warunek et al., "Physical and mechanical properties of elastomers in orthodontic positioners" *Am. J. Orthod. Dentofac. Orthop.* (1989) 95:388–400.

Wells, "Application of the positioner appliance in orthodontic treatment" *Am. J. Othodont.* (1970) 58:351–366.

* cited by examiner

SYSTEMS AND METHODS FOR POSITIONING TEETH

This application is related to Ser. No. 09/313,291, entitled "System and Method for Determining Final Position of Teeth," filed May 13, 1999 now U.S. Pat. No. 6,406,292; and Ser. No. 09/556,022, entitled "System and Method for Determining Final Position of Teeth," filed Apr. 20, 2000 now U.S. Pat. No. 6,457,972.

BACKGROUND

The present invention is related generally to the field of orthodontics, and more particularly to systems and methods for positioning teeth.

One objective in orthodontics is to move a patient's teeth to positions where the teeth function optimally and aesthetically. Conventionally, appliances such as braces are applied to the teeth of the patient by an orthodontist. Each appliance exerts continual forces on the teeth and gradually urges the teeth toward their ideal positions. Over a period of time, a treating professional such as an orthodontist adjusts the appliances to move the teeth toward their final destination.

Generally, the orthodontist specifies in a prescription the final tooth arrangement. The prescription is based on the orthodontist's knowledge and experience in selecting the intended final position of each tooth. The orthodontist or an assistant applies the treatment to move the teeth to their intended destination over a number of office visits. The process of attaching the braces to teeth is tedious and painful to the patient. Additionally, each visit reduces the "chair-time" available to the orthodontist that can be made available to another patient.

U.S. Pat. No. 5,975,893 entitled "Method and system for incrementally moving teeth," issued to Chishti, et al. on Nov. 2, 1999, and assigned to the assignee of the present invention, discloses a system for repositioning teeth with a plurality of individual appliances. The appliances are configured to be placed successively on the patient's teeth and to incrementally reposition the teeth from an initial tooth arrangement, through a plurality of intermediate tooth arrangements, and to a final tooth arrangement. The system of appliances is usually configured at the outset of treatment so that the patient may progress through treatment without the need to have the treating professional perform each successive step in the procedure.

Additionally, U.S. Pat. No. 6,406,292 filed May 13, 1999, entitled "System and Method for Determining Final Position of Teeth," and assigned to the assignee of the present invention, discloses an apparatus and method to define a fit for a set of upper and lower teeth in a masticatory system of a patient by generating a computer representation of the masticatory system of the patient; and determining an occlusion from the computer representation of the masticatory system using one or more keys. U.S. Pat. No. 6,457,972 filed Apr. 20, 2000, assigned to the assignee of the present invention, and entitled "System and Method for Determining Final Position of Teeth," shows a system, apparatus and computer-implemented method for arranging a computer model of teeth. According to one implementation, the method includes generating an archform representing an arrangement of teeth; placing a plurality of teeth according to the archform; determining a differential distance between each tooth and its neighbors; and moving each tooth according to the differential distance.

SUMMARY OF THE INVENTION

The present invention includes a system, apparatus and computer-implemented method for arranging a computer model of teeth.

In one aspect, a computer-implemented method produces appliances to treat teeth by specifying a sequence of tooth movements to move the teeth through a series of discrete tooth arrangements, wherein at least some of the tooth arrangements are represented by digital data sets; and producing one or more appliances in accordance with the digital data sets wherein the appliances comprise polymeric shells having cavities and wherein the cavities of successive shells have different geometries shaped to receive and resiliently reposition teeth from one tooth arrangement to a successive tooth arrangement.

Implementations of the above aspect may include one or more of the following. A sequence of tooth movements can be specified by moving teeth according to an optimization function, which can include force directed placement, simulated annealing, genetic algorithm, cost minimization, or a random walk algorithm. The sequence of tooth movements can cause the teeth to move until the sum of differential distances for the plurality of teeth exceeds a predetermined threshold, thereby producing a final digital data set. The sequence can include determining a first distance between a selected tooth and a first tooth that is adjacent to the selected tooth; determining a second distance between the selected tooth and a second tooth that is adjacent to the selected tooth; and calculating a difference between the first and second distances. The first and second distances can be the minimum distances between the teeth. The method can include generating an initial final digital data set based on a masticatory system of a patient; generating at least one intermediate digital data set based on the initial digital data set and the final digital data set; and producing an incremental adjustment appliance based on each intermediate digital data set.

The method also includes generating subsequent digital data sets based on prior digital data sets until a final digital data set representing an acceptable tooth arrangement is achieved. Additionally, the method includes generating an initial digital data set representing an initial tooth arrangement; based on the initial digital data set, generating a second data set representing a second tooth arrangement; and, based on the second data set, generating a third data set representing a third tooth arrangement.

In another aspect, an apparatus for producing appliances to treat teeth includes: means for generating a digital arrangement of teeth; means for specifying a sequence of tooth movements to move the teeth to a target arrangement; and means for generating one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

In yet another aspect, a computer program product, tangibly stored on a computer-readable medium, for producing appliances to treat teeth, includes instructions operable to cause a programmable processor to: generate a digital arrangement of teeth; specify a sequence of tooth movements to move the teeth to a target arrangement; and generate one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

In yet another aspect, a system for treating teeth includes a processor; a display device coupled to the processor; and a data storage device coupled to the processor, the data storage device storing instructions operable to cause the processor to: generate a digital arrangement of teeth; specify a sequence of tooth movements to move the teeth to a target arrangement; and generate one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

Advantages of the invention include one or more of the following. When a prescription or other final designation is provided, a computer model can be generated and manipulated to match the prescription. The prescription may be automatically interpreted in order to generate an image as well as a digital data set representing the final tooth arrangement.

DESCRIPTION

Figure 1:
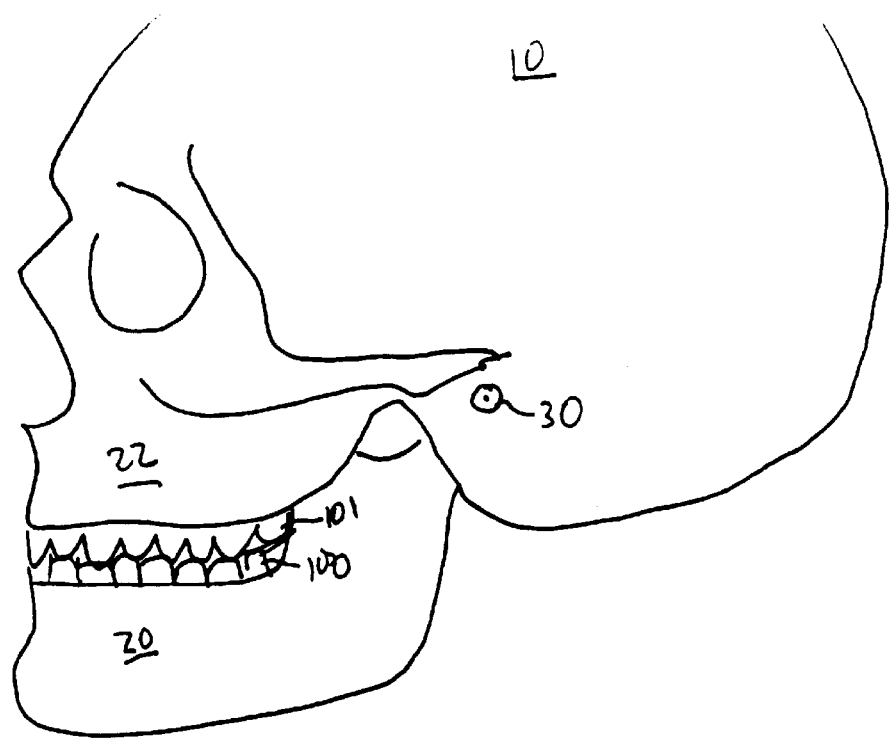
FIG. 1 is an elevational diagram showing the anatomical relationship of the jaws of a patient.

FIG. 1 shows a skull 10 with an upper jaw bone 22 and a lower jaw bone 20. The lower jaw bone 20 hinges at a joint 30 to the skull 10. The joint 30 is called a temporal mandibular joint (TMJ). The upper jaw bone 22 is associated with an upper jaw 101, while the lower jaw bone 20 is associated with a lower jaw 100. A computer model of the jaws 100 and 101 is generated in accordance with the process of FIG. 3, and a computer simulation can model interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
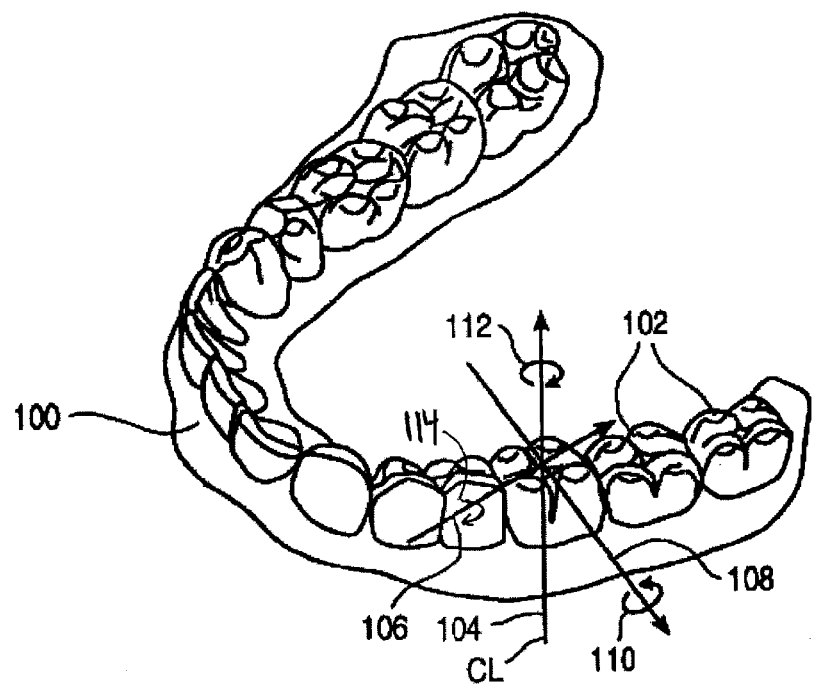
FIG. 2A illustrates in more detail the patient's lower jaw and provides a general indication of how teeth may be moved by the methods and apparatus of the present invention.

Referring now to FIG. 2A, a visual representation of the digital data representing the computer model of the lower jaw 100 includes a plurality of teeth 102, for example. At least some of these teeth may be moved by the methods of the present invention from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 114. Thus, all possible free-form motions of the tooth can be performed.

Figure 2B:
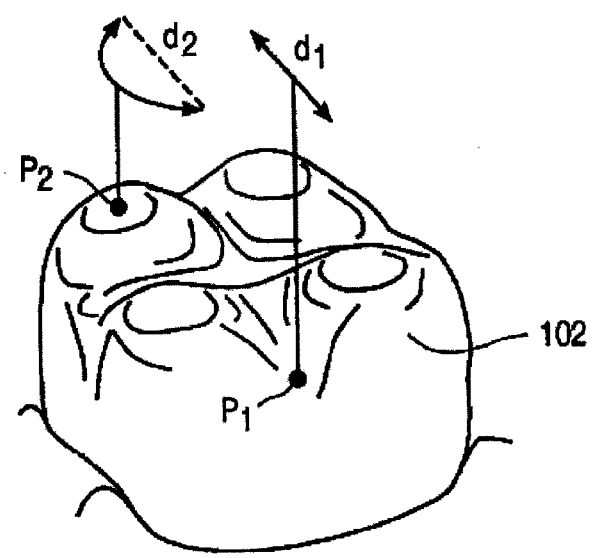
FIG. 2B illustrates a single tooth from FIG. 2A and defines how tooth movement distances are determined.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
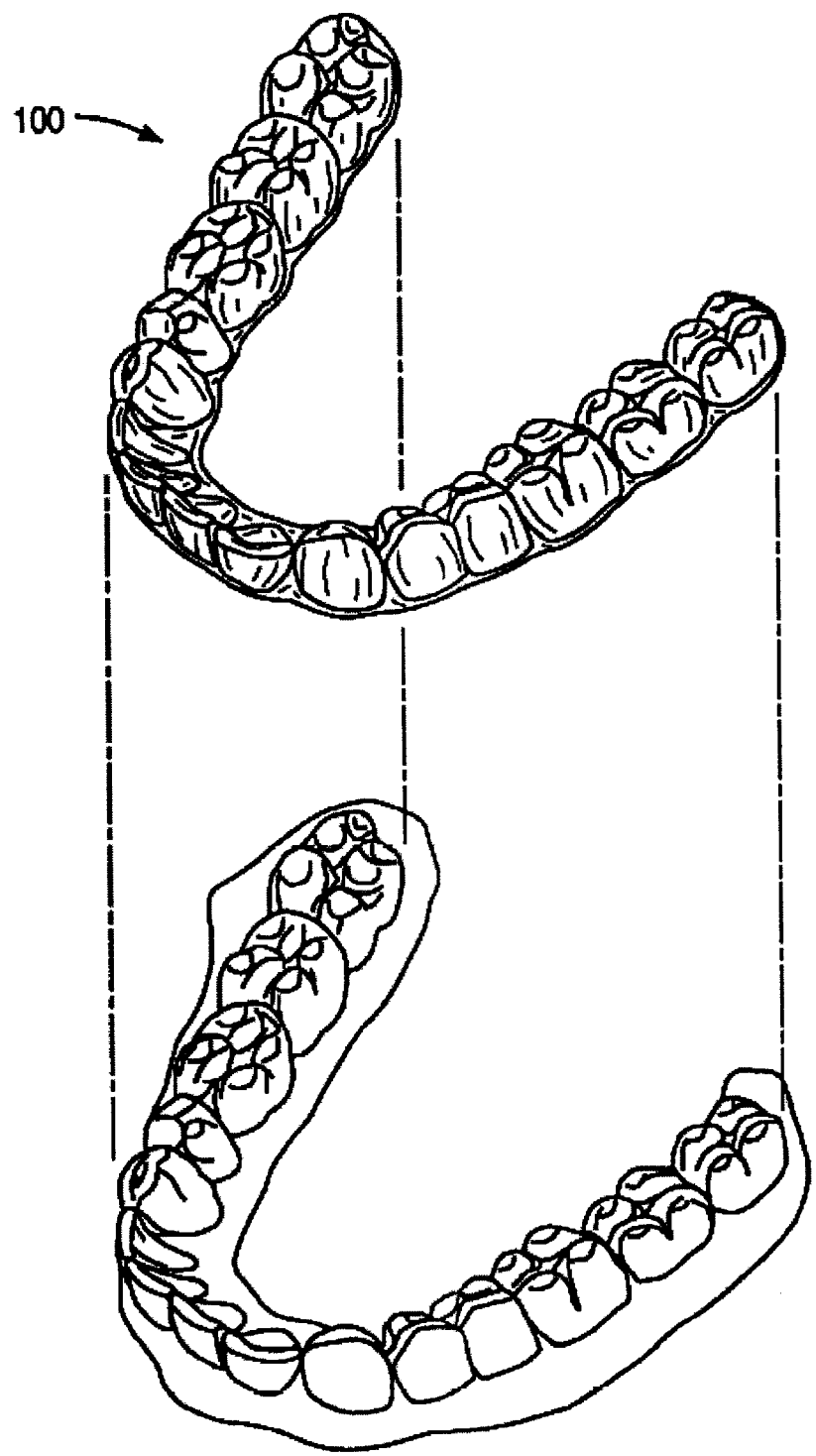
FIG. 2C illustrates the jaw of FIG. 2A together with an incremental position adjustment appliance.

FIG. 2C shows one adjustment appliance 111 which can be worn by the patient in order to achieve an incremental repositioning of individual teeth in the jaw as described generally herein. The appliance is a polymeric shell having a teeth-receiving cavity, as described in U.S. Pat. No. 5,975,893, entitled "Method and system for incrementally moving teeth," the full disclosures of which are incorporated by reference. Various improvements in and modifications to the appliances are described in copending application Ser. No. 09/250,962, filed on Feb. 16, 1999, entitled "System and method for releasing tooth positioning appliances"; Ser. No. 09/454,278, filed Dec. 3, 1999, entitled "Attachment devices and methods for a dental applicant"; Ser. No. 09/454,786, filed Dec. 3, 1999, entitled "Manipulable dental model system for fabrication of a dental appliance"; Ser. No. 09/483,071, filed Jan. 14, 2000, entitled "System and method for producing tooth movement"; Ser. No. 09/616, 222, filed Jul. 14, 2000, entitled "Embedded features and methods of a dental appliance"; Ser. No. 09/666,783, filed Sep. 21, 2000, entitled "Methods and systems for concurrent tooth repositioning"; Ser. No. 09/616,830, filed Jul. 14, 2000, entitled "Systems and methods for varying elastic modulus appliances"; and Ser. No. 09/658,340, filed Sep. 8, 2000, entitled "Modified tooth positioning appliances and methods and systems," the full disclosures of which are incorporated herein by reference.

As set forth in the prior patents and applications, each polymeric shell may be configured so that its tooth-receiving cavity has a geometry corresponding to an intermediate or final tooth arrangement intended for the appliance. The patient's teeth are repositioned from their initial tooth arrangement to an intermediate and/or a final tooth arrangement by placing a series of incremental position adjustment appliances over the patient's teeth. At least one of the appliances used in a single course of treatment is preferably generated at the beginning of the treatment so that they are available when needed. The remaining appliances can be produced when needed so that the efficiency of the fabrication process is enhanced. The patient wears each appliance until the pressure applied by each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth, but wires and other devices can be affixed to the appliance to achieve certain capabilities, e.g., as described in the above incorporated-by-reference applications. In some cases, however, it will be desirable or necessary to provide individual anchors on teeth with corresponding receptacles or apertures in the appliance 100 so that the appliance can apply an upward force on the tooth that would not be possible in the absence of such an anchor.

Figure 3:
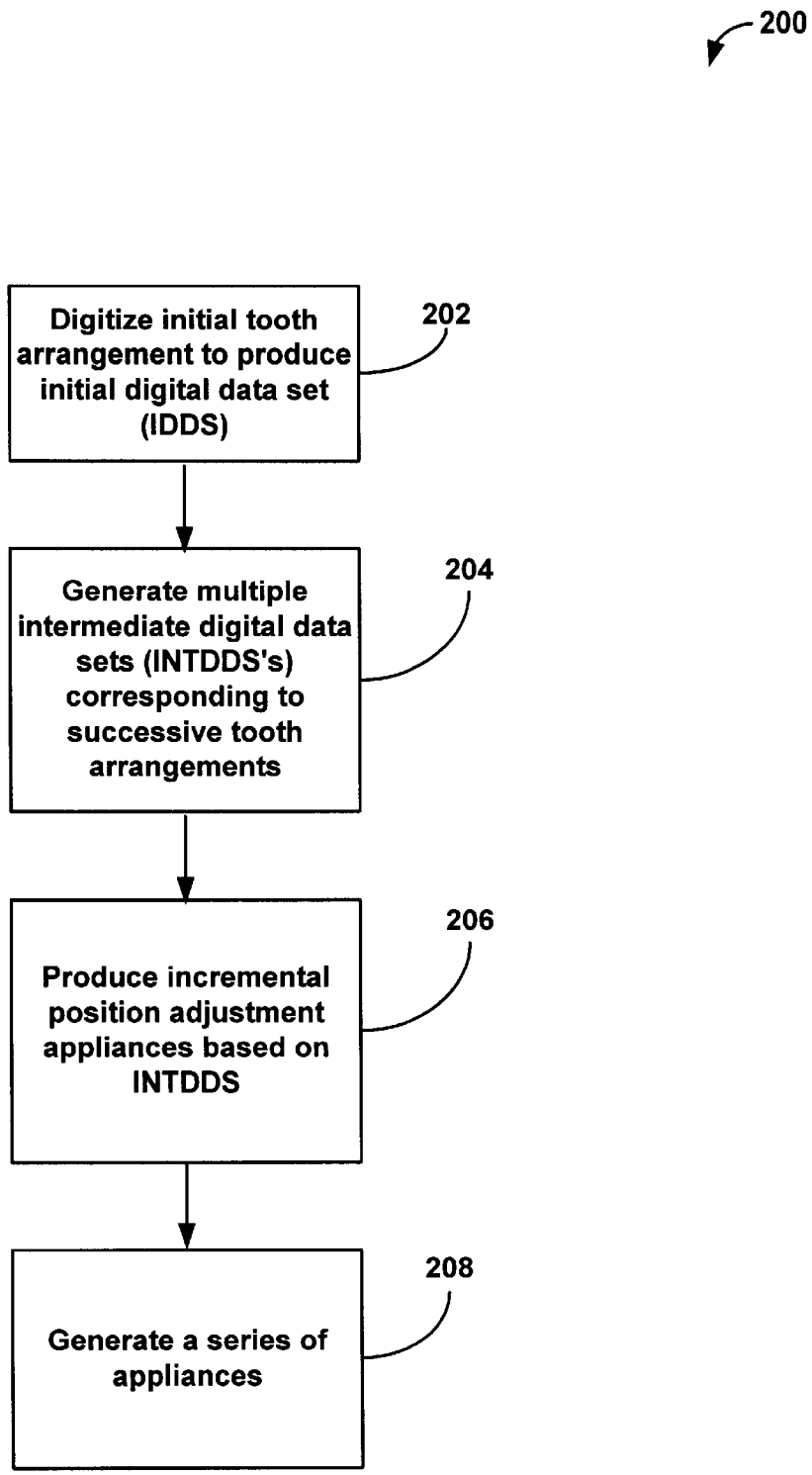
FIG. 3 is a block diagram illustrating a process for producing incremental position adjustment appliances.

FIG. 3 shows a process 200 for producing the incremental position adjustment appliances for subsequent use by a patient to reposition the patient's teeth. The flow chart of FIG. 3 is for purpose of explanation and does not necessarily reflect all possible paths of control flow in the execution of the client program.

As a first step, an initial digital data set representing an initial tooth arrangement is obtained (step 202). The initial data set may be obtained in a variety of ways. For example, the patient's teeth may be scanned or imaged using X-rays, three dimensional X-rays, computer-aided tomographic images or data sets, or magnetic resonance images, among others. The teeth data may be generated by a destructive scanner, as described in the incorporated-by-reference U.S. application Ser. No. 09/169,034, filed Oct. 8, 1998, and provisional application Ser. No. 60/235,240 filed on Sep. 25, 2000, the full disclosure of which is also incorporated herein by reference. The initial data set is then manipulated using a computer having a suitable graphical user interface (GUI) and software appropriate for viewing and modifying the images. Individual tooth and other components may be segmented or isolated in the model to permit their individual repositioning or removal from the digital model. The existing position of the teeth is used as the starting position. The ending position can be determined algorithmically, or can be specified in the prescription written by the orthodontist or treating professional.

After segmenting or isolating the components, the teeth are moved based on rules and algorithms programmed into the computer (step 206). In one embodiment, positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement, which is customized to the patient's teeth, as discussed below. After applying the ideal model to the computer representation, the position of the teeth can be optimized to fit the ideal model. The ideal model may be specified by one or more arch forms, or may be specified using various features associated with the teeth.

In one implementation, each stage of tooth movement is determined by an attraction model between selected points on adjacent teeth. This step is iterated until an acceptable result is achieved. In this manner, subsequent digital data sets based on prior digital data sets are iteratively generated until a final digital data set representing an acceptable tooth arrangement is achieved. In one embodiment, the sequence of tooth movements can be arrived at by generating an initial digital data set representing an initial tooth arrangement. Based on the initial digital data set, a second data set representing a second tooth arrangement can be generated; and, based on the second data set, a third data set representing a third tooth arrangement can be generated.

The system stops the movement when the relative positions of the teeth satisfy a predetermined target. In one example, the target is reached when the teeth fit the prescribed position without any inter-teeth gap. In another example, the target is reached when the teeth reaches the ending position as prescribed by the orthodontist or treating professional.

In another implementation, a series of teeth movements are generated using an optimization function or process. In this implementation, the teeth placement is determined such that the teeth fits an ideal archform determined by the prescription or any other specification, and the total gap between teeth and number of teeth movement stages are minimized. The implementation can generate one or more initial placements, modifying the placements using optimization methodologies including force directed placement or simulated annealing, random walk, constructive placement, or Genetic Algorithms such as simulated evolution, and comparing the resulting placements using one or more cost or other criteria. The system solves an optimization problem with each teeth stage whose configuration is specified by a set of numbers. A "cost" function is evaluated for any given set of values for the numbers; and the "optimum" configuration is that which has the minimum cost over all possible assignments of values to the set of numbers.

Once the teeth arrangements are determined, a series of appliances that move the teeth in a specified sequence are generated (step 208). For example, the teeth models may be rotated until their roots are in the proper vertical position. Next, the teeth models may be rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together can be visualized using a collision detection process to highlight the contacting points of the teeth.

Figure 4:
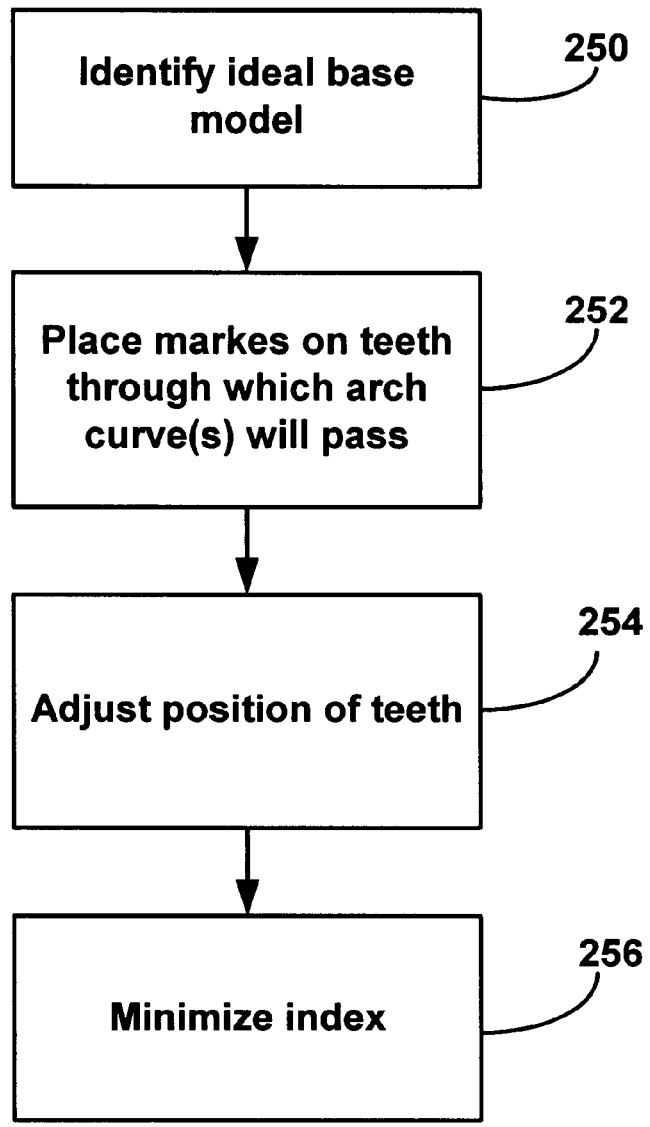
FIG. 4 is a flow chart illustrating a process for optimizing a final placement of the patient's teeth.

FIG. 4 is a flow chart illustrating a process for determining final position of the patient's teeth. The process of FIG. 4 identifies an ideal base model for the final position of the teeth that consists of an arch curve (step 250). This model can be selected from a suite of template models, derived from patients with ideal occlusion, or derived from patient under treatment (using casts, X-rays, a prescription, or data about the patient from other sources). Next, the user of the software places and orients a marker on each tooth, through which the arch curve (or curves) is intended to pass (step 252). The curves can be designed so that they should pass through markers placed on the tooth's facial, lingual, or occlusal surface. Multiple arch curves can be used to make the specification of the final position more accurate. In step 254, the position and orientation of the teeth are adjusted so that the arch curve passes through the marker on each tooth and the teeth do not overlap. Optionally, the teeth can be made to contact each other in this step. Next, the position and orientation of the tooth is set based on minimizing one or more indices or features (step 256). In another implementation, the markers can be automatically placed and oriented on each tooth.

In one embodiment, the user can optionally adjust their position and orientation. For example, the process can accept as input an initial digital data set as described above, and generate a final digital data set automatically. A user can examine the output of the process, make adjustments, and execute the process again. Example adjustments include changing the shape of the archform, moving teeth, and changing the orientation of teeth by adjusting tip, inclination, and the like. The embodiment generates an archform, which can be selected from among a set of arch templates or can be entered manually. The archform can be planar or according to a curve of Spee. The archform can be adjusted manually by a user. Teeth are then placed on the archform. To facilitate user adjustment, each tooth includes an attachment point. The attachment point can be on any surface of the tooth, or within the tooth. The teeth are placed so that the archform passes through each attachment point.

Figure 5:
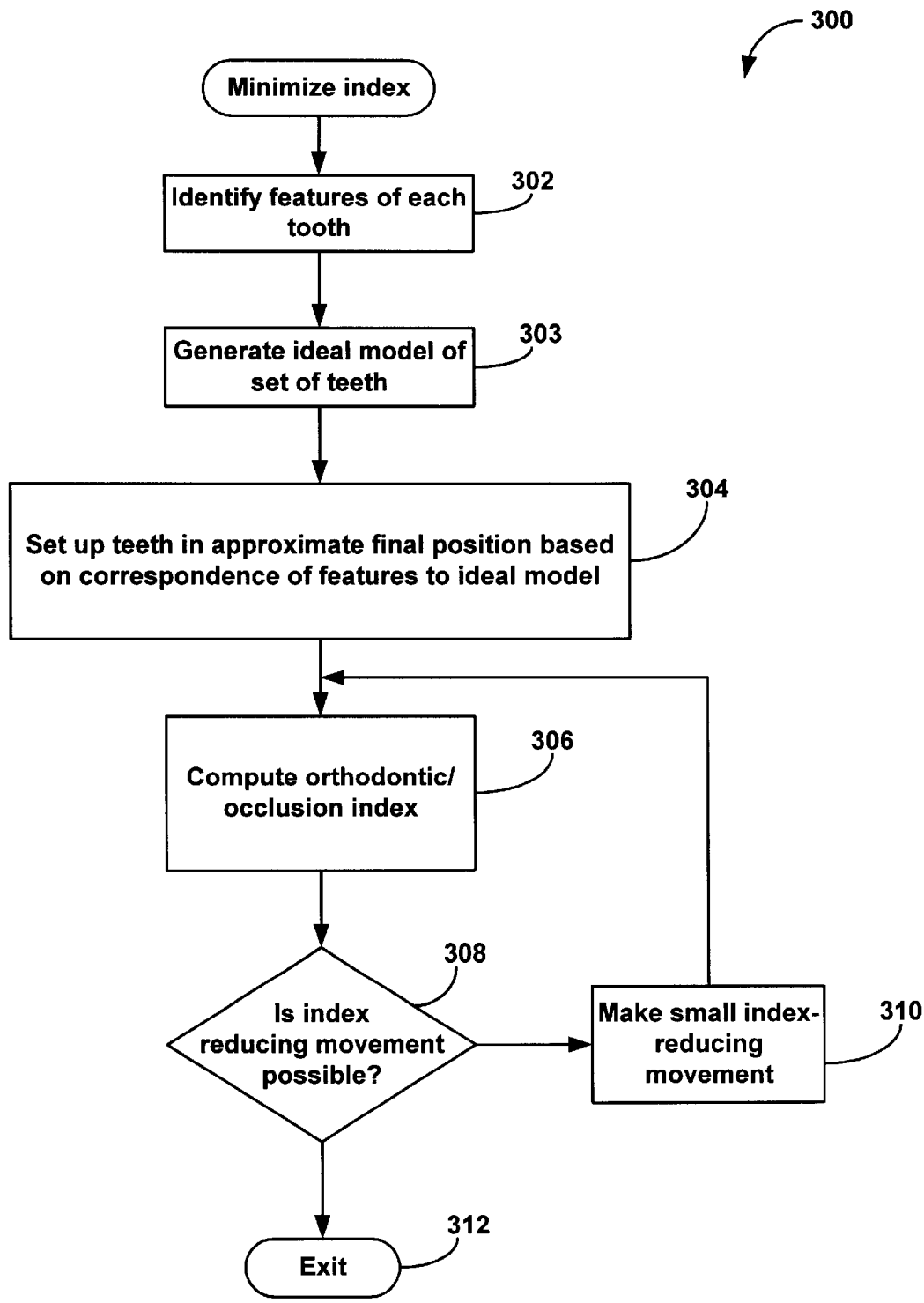
FIG. 5 is a flow chart illustrating a process for performing functional occlusion on the patient's teeth.

FIG. 5 illustrates a process 300 that optimizes the placement of the teeth based on teeth features. First, the process 300 automatically or, with human assistance, identifies various features associated with each tooth to arrive at a model of the teeth (step 302). An ideal model set of teeth is then generated either from casts of the patient's teeth or from patients with a good occlusion (step 303). From step 302, the process 300 positions the model of the teeth in its approximate final position based on a correspondence of features to the ideal model (step 304). In that step, each tooth model is moved so that its features are aligned to the features of a corresponding tooth in the ideal model. The features may be based on cusps, fossae, ridges, distance-based metrics, or shape-based metrics. Shape-based metrics may be expressed as a function of the patient's arches, among others. For example, cusp features associated with each tooth may be used. Cusps are pointed projections on the chewing surface of a tooth. In a detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth. The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as a flood fill step. From each candidate cusp point, outward flooding is performed, marking each vertex on the model visited in this matter as part of the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance. After the detection stage, the cusp detection process may include a rejection stage where local geometries around each of the cusp candidates are analyzed to determine if they possess non-cusp-like features. Cusp candidates that exhibit non-cusp-like features are removed from the list of cusp candidates. Various criteria may be used to identify non-cusp-like features. According to one test, the local curvature of the surface around the cusp candidate is used to determine whether the candidate possesses non-cusp-like features. Alternatively, a measure of smoothness is computed based on the average normal in an area around the candidate cusp. If the average normal deviates from the normal at the cusp by more than a specified amount, the candidate cusp is rejected. Next, the process 300 computes an orthodontic/occlusion index (step 306).

One index which may be used is the PAR (Peer Assessment Rating) index. In addition to PAR, other metrics such as shape-based metrics or distance-based metrics may be used. The PAR index identifies how far a tooth is from a good occlusion. A score is assigned to various occlusal traits which make up a malocclusion. The individual scores are summed to obtain an overall total, representing the degree a case deviates from normal alignment and occlusion. Normal occlusion and alignment is defined as all anatomical contact points being adjacent, with a good intercuspal mesh between upper and lower buccal teeth, and with nonexcessive overjet and overbite. In PAR, a score of zero would indicate good alignment, and higher scores would indicate increased levels of irregularity. The overall score is recorded on pre- and posttreatment dental casts. The difference between these scores represents the degree of improvement as a result of orthodontic intervention and active treatment. The eleven components of the PAR Index are: upper right segment; upper anterior segment; upper left segment; lower right segment; lower anterior segment; lower left segment; right buccal occlusion; overjet; overbite; centerline; and left buccal occlusion. In addition to the PAR index, other indices may be based on distances of the features on the tooth from their ideal positions or ideal shapes. From step 306, the process 300 determines whether additional index-reducing movements are possible (step 308). Here, all possible movements are attempted, including small movements along each major axis as well as small movements with minor rotations.

An index value is computed after each small movement and the movement with the best result is selected. In this context, the best result is the result that minimizes one or more metrics such as PAR-based metrics, shape-based metrics or distance-based metrics. The optimization may use a number of techniques, including simulated annealing technique, hill climbing technique, best-first technique, Powell method, and heuristics technique, among others. Simulated annealing techniques may be used where the index is temporarily increased so that another path in the search space with a lower minimum may be found. However, by starting with the teeth in an almost ideal position, any decrease in the index should converge to the best result. In step 308, if the index can be optimized by moving the tooth, incremental index-reducing movement inputs are added (step 310) and the process loops back to step 306 to continue computing the orthodontic/occlusion index. Alternatively, in the event that the index cannot be optimized any more, the process 300 exits (step 312).

Figure 6:
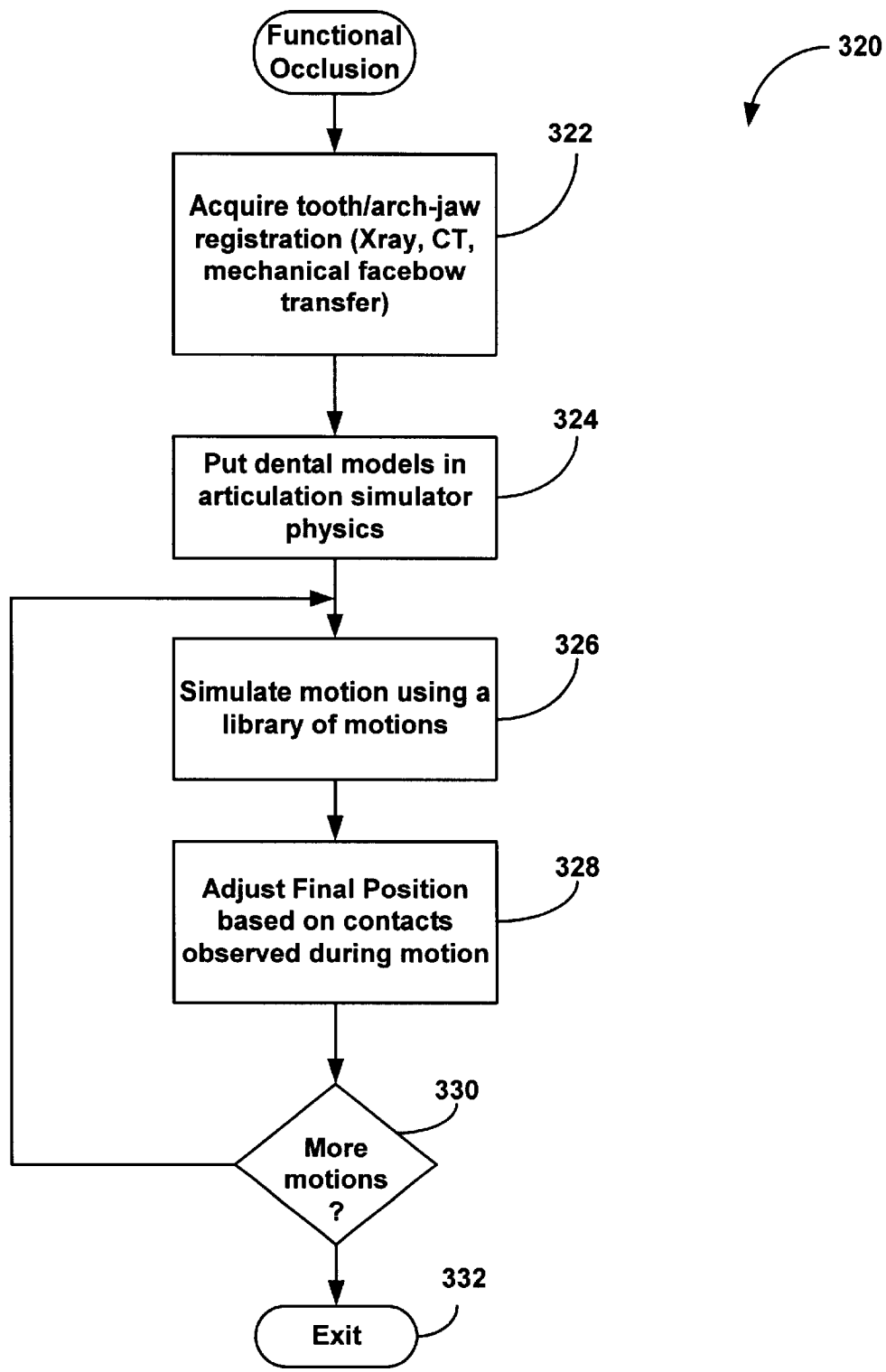
FIG. 6 is a flow chart illustrating an optional process for incorporating mid-treatment information to the final placement of the patient's teeth.

Turning now to FIG. 6, a process 320 for performing functional occlusion is shown. Functional occlusion is a process for determining how well the teeth fit together when the jaws move. The process 320 first acquires tooth/arch jaw registration. This may be done using conventional techniques such as X-ray, a computer tomography, or a mechanical device such as a face bow transfer. After acquiring the registration information, the process 320 places digital dental models of the teeth in a digital articulation simulator (step 324). The articulation simulator allows a subset of jaw movements such as bite-movements to be simulated, as described below. From step 324, the process 320 simulates jaw motions (step 326). A simplified set of movement physics (kinematics) is applied to the dental models. The process 320 performs a simulation using a simplified set of interacting forces on the jaws 100 and 101 in relation to one another. The simplified physical simulation allows the system to focus on motions involving much contact between the jaws.

The physical simulation allows the system to render realistic physically correct jaw movements when the jaws 100 and 101 come into contact with each other. A range of simulated motion may be supplied using a library of motions. One typical motion supplied by the library is a protrusive motion where the lower jaw 101 is moved forward and backward to bring the front teeth on both jaws into contact with each other. Another motion is a lateral motion found in food chewing. The lateral motion involves moving the jaws 100 and 101 side to side. Other motions that may be supplied in the library include motions that are "tooth guided" where the path of the lower jaw 100 is guided by the teeth in contact with each other. Next, the process 320 adjusts the final position based on contacts observed during the simulation of motions in step 326 (step 328). The result of the simulation is analyzed, the position of each tooth can be adjusted if contacts associated with that tooth are deemed excessive. Finally, based on the contact data generated, the process determines whether additional motion simulations need to be done. The motion simulation may be rerun until the contacts associated with each tooth are acceptable to the treating orthodontist. The tooth model manipulation process can be done subjectively, i.e., the user may simply reposition teeth in an aesthetically and/or therapeutically desired manner based on observations of the final position or based on the simulation of contacts. Alternatively, rules and algorithms may be used to assist the user in repositioning the teeth based on the contacts. If the simulation needs to be repeated, the process loops back to step 326 (step 330). Alternatively, the process exits (step 332).

Figure 7:
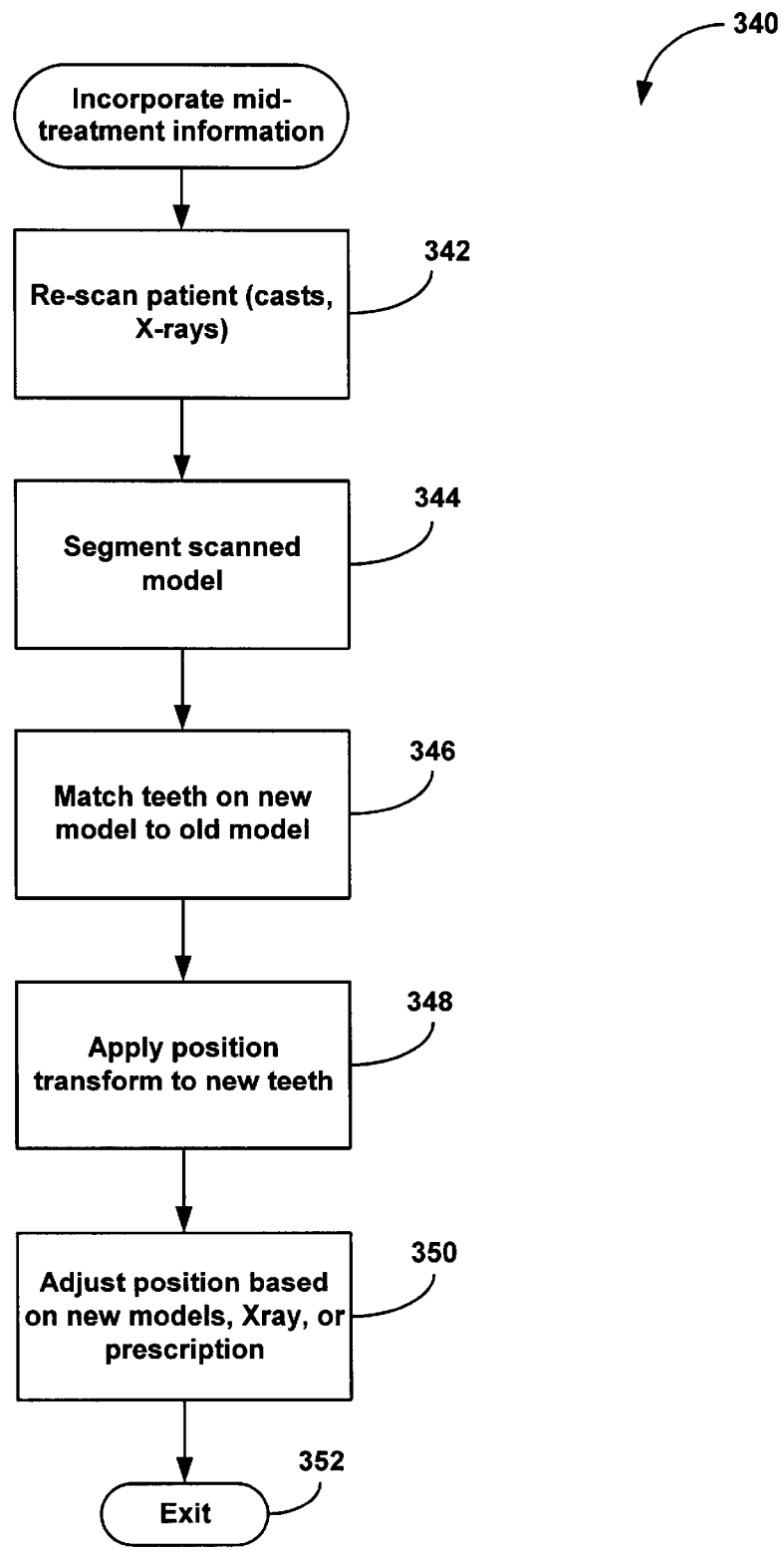
FIG. 7 is flow chart illustrating a process for optimizing occlusion based on one or more keys.

FIG. 7 shows an optional process of 340 of incorporating midtreatment information to the final positioning process. First, a digital model incorporating dental information associated with the patient is generated from a scan of the patient's teeth (step 342). The scan may be performed using casts, X-rays or any of the conventional scanning methods. Next, the digital model is segmented into one model for each tooth (step 344). Each tooth is then matched against a model associated with a prior scan developed at the beginning of the treatment plan (step 346). The matching process is based on matching corresponding points between the current scan and the prior scan of the teeth. In most cases, the teeth segmented from the current scan retain the shapes determined at the beginning of the treatment plan, and the matching process is easy because the models should be similar to each other. A final position transform is then applied to the new teeth model (step 348). The final position and specification from the prior model is copied to the current model of the patient, and the final position is adjusted based on the new models, the new X-ray information or a new prescription (step 350). Step 350 basically involves rerunning the minimization process 300 (FIG. 4) described previously with the new information, which may be a slight change in the model, a change in the X-ray scan, or a change the prescription. Finally, the process 340 exits (step 352)

Figure 8:
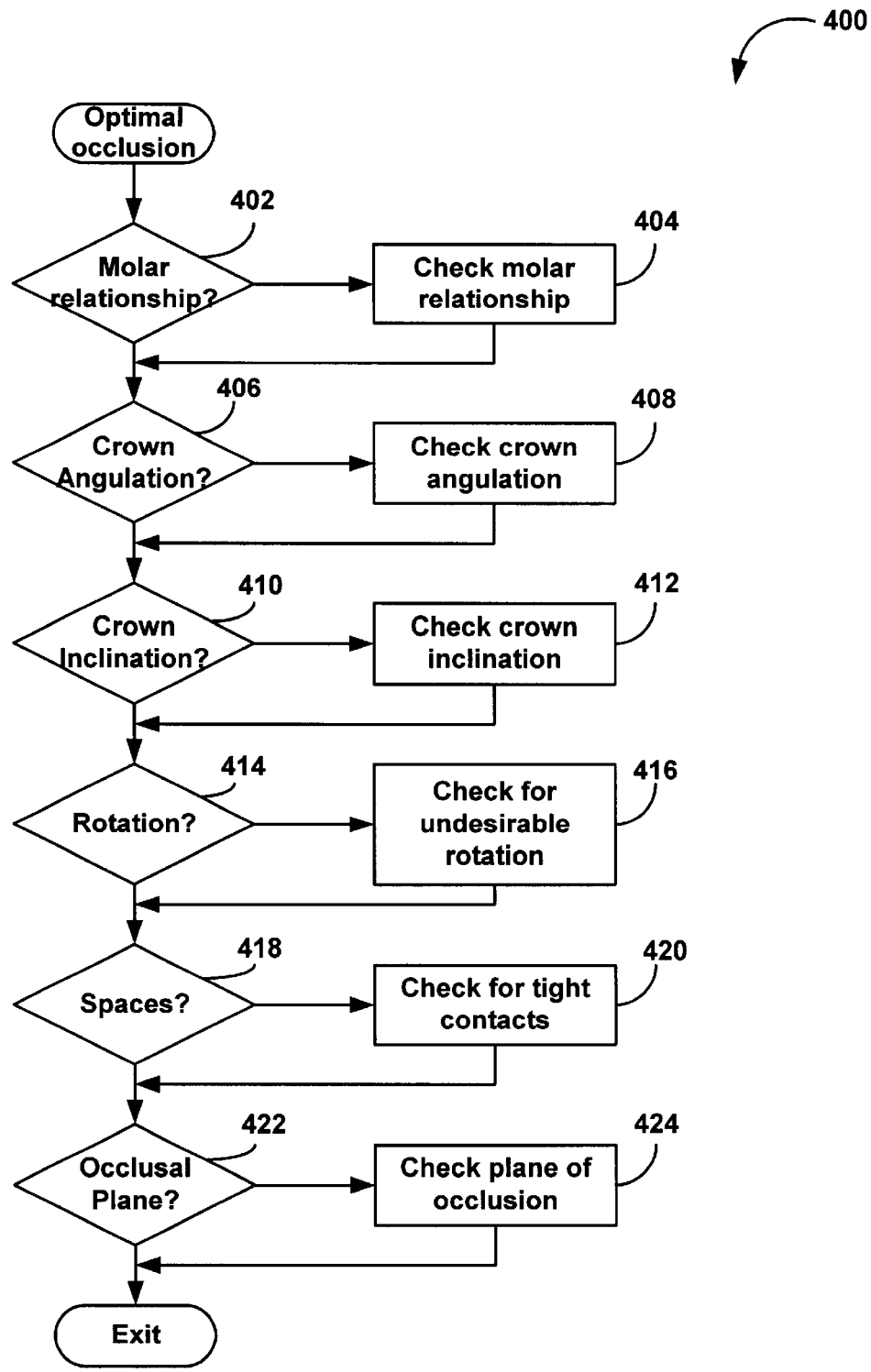
FIG. 8 is a flow chart illustrating a second process for performing functional occlusion on the patient's teeth.

FIG. 8 is a flowchart of one embodiment of a process 400 for determining optimal occlusion in the teeth model. The process 400 optimizes the occlusion based on six characteristics (Six Keys) that were found to be consistently present in a collection of 120 casts of naturally optimal occlusion. The keys include a molar relationship key, a crown angulation key, a crown inclination key, teeth rotation key, teeth contact point key, and an occlusal plane key. The individual keys provide a complete set of indicators of optimal occlusion, can be judged from tangible landmarks, and can be judged from a facial and occlusal surfaces of the crowns, thus reducing the need for a lingual view for articulating paper to confirm occlusial interfacing. These keys are described in Lawrence F. Andrews, "The six keys to normal occlusion," Am. J. Orthod. Vol. 62, No. 3 pp. 296–309 (September 1972) and in Chapter 3 of his book entitled "Straight Wire—The Concept and Appliance" (Published by L. A. Wells), the contents of which are incorporated by reference. The Six Keys are interdependent elements of the structural system of optimal occlusion and are based on similarities in the patterns of angulation, inclination, shape, and relative size (facial prominence) of tooth types. As such, they serve as a basis for evaluating occlusion. The Six Keys are used as treatment objectives for patients. The characteristics of the Six Keys are incorporated into the design of appliance 111 to enhance precision and consistency in treatment results. The process 400 first checks whether optimization is to be done with respect to a molar relationship key (step 402). If so, the process 400 checks and applies an appropriate molar relationship (step 404). The molar relationship pertains to the occlusion and the interarch relationships of the teeth. Step 404 enforces the following seven requirements of the molar relationship key:

1. The mesiobuccal cusp of the permanent maxillary first molar occludes in the groove between the mesial and the middle buccal cusps of the permanent mandibular first molar.
2. The distal marginal ridge of the maxillary first molar occludes with the mesial marginal ridge of the mandibular second molar.
3. The mesiolingual cusp of the maxillary first molar occludes in the central fossa of the mandibular first molar.

4. The buccal cusps of the maxillary premolars have a cusp-embrasure relationship with the mandibular premolars.
5. The lingual cusps of the maxillary premolars have a cusp-fossa relationship with the mandibular premolars.
6. The maxillary canine has a cusp-embrasure relationship with the mandibular canine and first premolar. The tip of its cusp is slightly mesial to the embrasure.
7. The maxillary incisors overlap the mandibular incisors and the midlines of the arches match.

The cusp-groove and the marginal-ridge conditions of the molars, the cusp-embrasure relationship of the premolars and canines, and incisor overjet can be observed directly from the buccal perspective. A facial axis of the clinical crown (FACC) measurement is used to permit assessment of the lingual-cusp occlusion of the molars and premolars when these teeth are viewed from their mesiobuccal aspect, as explained below. In step 404, interarch relationship of the posterior teeth of two dentitions can be the same, but the interfacing of the occlusal surfaces of the two dentitions may differ because of differing crown inclinations. Step 404 ensures that correct occlusal interfacing through correct interarch relationship, angulation, and crow inclination. Interarch relationship and angulation are best judged from the buccal perspective; crown inclination for posterior teeth is best judged from the dentition's mesiobuccal perspective. Judging posterior occlusion first from the buccal (for angulation and interarch relationship) then from the mesiobuccal (for inclination) provides a perspective that can be systematically described and quantified. Such information, along with other nonocclusal guidelines, are used in step 404 to identify occlusal deviations. Step 404 includes occluding a first permanent molar with a second permanent molar. In such an occlusion, the first permanent molar has a distobuccal cusp with a distal surface, the second permanent molar has a mesiobuccal cusp with a mesial surface and the distal surface occludes with the mesial surface. The mesiobuccal cusp can occlude in a groove between mesial and middle cusps of the first permanent molar. The mesial surface can closely approach the distal surface. Moreover, where the teeth have canines and premolars, the canines and premolars have a cusp-embrasure relationship buccally and a cusp-fossa relationship lingually.

From step 402 to 404, the process 400 checks whether the occlusion needs to be optimized with respect to a crown angulation key (step 406). If so, the occlusion is optimized with respect to the crown angulation key (step 408). Essentially, step 408 ensures that all crowns should have a positive angulation, and all crowns of each tooth type should be similar in the amount of angulation. Further, the contact-area position for each tooth type should be similar. Step 408 determines a distal inclination of a gingival portion of the crown. The distal inclination may be constant within each tooth type. The angulation may be determined between the FACC and a line perpendicular to an occlusal plane. Step 408 may minimize the angulation, which may be positive or negative. From step 406 or step 408, the process 400 checks whether the occlusion is to be optimized with respect to a crown inclination key (step 410). If so, the crown inclination optimization is performed (step 412). As they do in angulation, consistent patterns also prevail in crown inclination, the following three characteristics for individual teeth are analyzed in step 412.

1. Most maxillary incisors have a positive inclination; mandibular incisors have a slightly negative inclination. In most of the optimal sample, the interincisal crown angle is less than 180E. The crowns of maxillary incisors are more positively inclined, relative to a line 90E to the occlusal plane, than the mandibular incisors are negatively inclined to the same line.
2. The inclinations of the maxillary incisor crowns are generally positive—the centrals more positive than the laterals. Canines and premolars are negative and quite similar. The inclinations of the maxillary first and second molars are also similar and negative, but slightly more negative than those of the canines and premolars. The molars are more negative because they are measured from the groove instead of from the prominent facial ridge, from which the canines and premolars are measured.
3. The inclinations of the mandibular crowns are progressively more negative from the incisors through the second molars.

In step 412, the crown inclination can represent an angle formed by a line perpendicular to an occlusal plane and a line tangent to a bracket site. In this step, the crown inclination can be negative when measured from an upper canine through an upper second premolar. The crown inclination may become progressively more negative when measured from a lower canine through a lower second molar. The crown inclination may also be positioned between a line parallel and tangent to the FACC at its midpoint and a line perpendicular to an occlusal plane. From step 410 or 412, the process 400 checks whether the occlusion is to be optimized using a rotation key (step 414). If so, the process 400 checks for undesirable rotations (step 416) and corrects the model so that tooth rotations are absent. From step 414 or step 416, the process 400 then determines whether the occlusion needs to be optimized with respect to spacing (step 418). If so, the process 400 checks for tight contacts that is, no spaces should exist between teeth (step 420). Step 418 checks that contact points abut unless a discrepancy exists in mesiodistal crown diameter. From step 418 or step 420, the process 400 then checks whether the occlusion is to be optimized with respect to an occlusal plane key (step 422). If so, the process 400 then optimizes the teeth model by analyzing the plane of occlusion (step 424). In step 424, the depth of the curve of Spee ranges from a flat plane to a slightly concave surface. The plane can range between flat to curves of Spee. Moreover, the curve of Spee may be deep, slight, or reversed. From step 422 or step 424, the process 400 exits.

Figure 9:
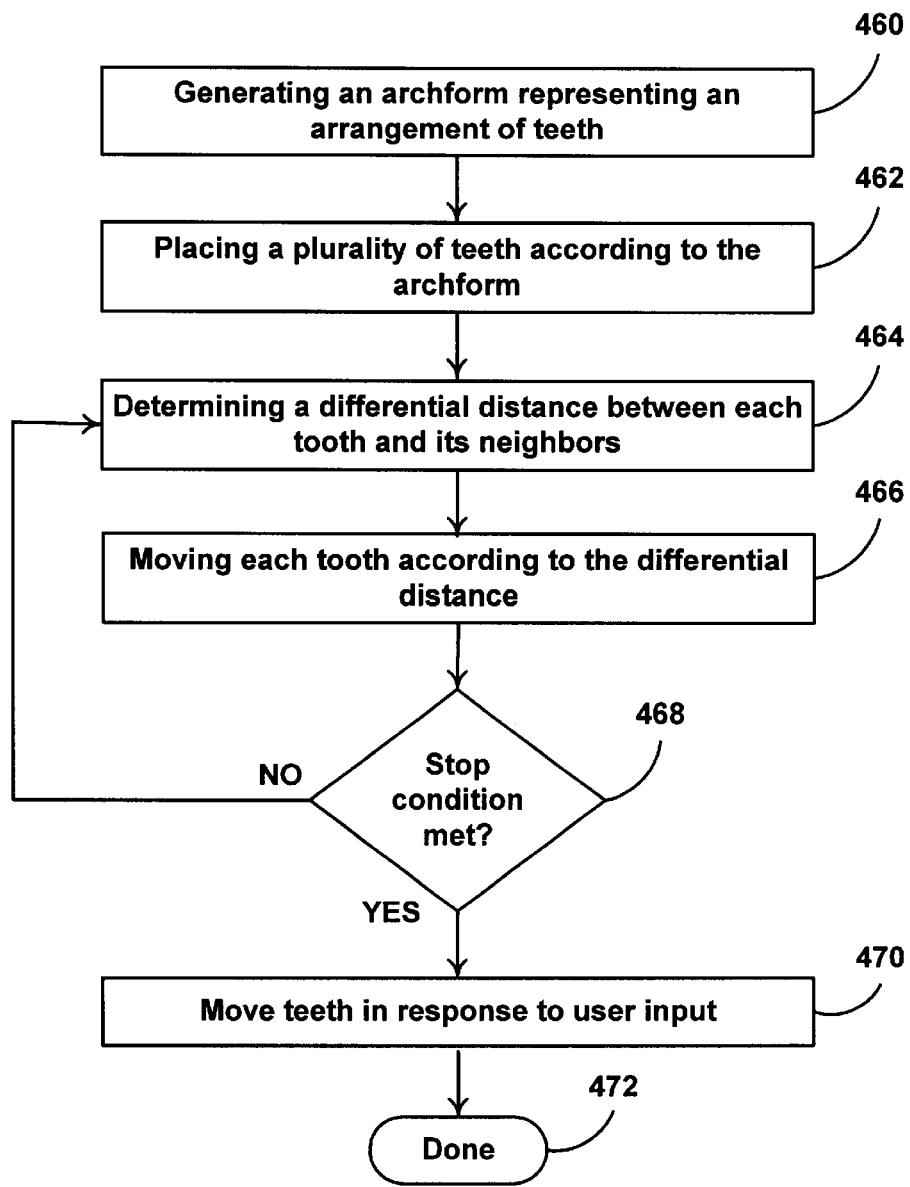
FIG. 9 is a flow chart illustrating one embodiment of a process for moving teeth with human assistance.

FIG. 9 is a flow chart illustrating one embodiment of a process for moving teeth with human assistance. Step 460 commences with generating an archform that represents an arrangement of teeth. The process moves onto step 462 which places a plurality of teeth according to the archform. Step 464 then determines a differential distance between each tooth and its neighbors, with step 466 moving each tooth according to the differential distances determined in step 464. At 468, the stop condition is evaluated. If it has not been met, then the process loops back to step 464. If it has been met, then step 470 reflects that the tooth have been moved in response to user input and exits at step 472. An exemplary computer model of teeth with attachment point and an exemplary diagram illustrating how the attachment point is used to move teeth are discussed in more detail in FIGS. 10 and 11 below.

The process of FIG. 9 moves each tooth according to its differential distance (step 466). Each tooth is translated and oriented so that the attachment point of the tooth remains on the archform. Each tooth is translated a distance proportional to its differential distance. The process repeats until a stop condition is met (step 468), thereby producing a proposed digital data set. In one implementation, the stop condition is met when the sum of differential distances for the teeth falls below a predetermined threshold. Of course, other stop conditions can be used, such as limiting the number of iterations to be performed. In one implementation, three-dimensional distance vectors are used.

Figure 10:
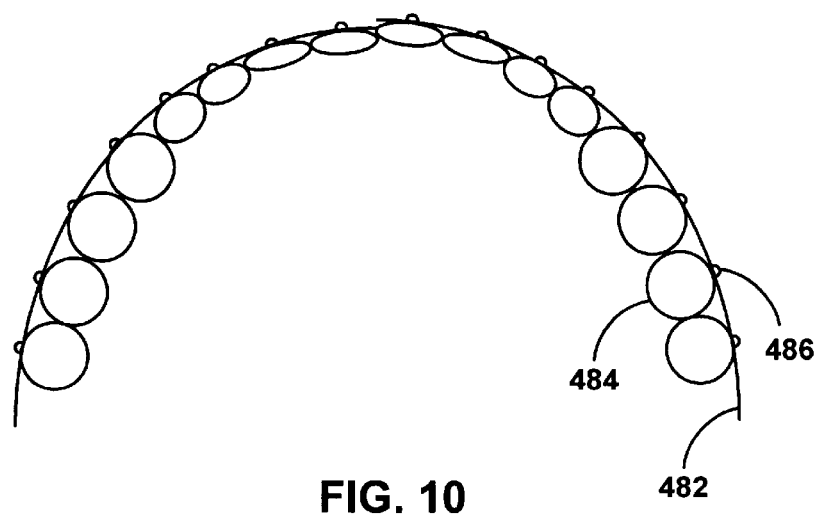
FIG. 10 depicts a computer model of a patient's teeth with an attachment point to digitally move the teeth.

FIG. 10 depicts a computer model of teeth. A plurality of teeth 484, each having a labial attachment point 486, is placed such that the archform 482 passes through each attachment point. In one embodiment, a differential distance between each tooth and its neighbors is used as an index to move the teeth. The differential distance for a selected tooth is obtained by determining the distances between the selected tooth and the teeth that are adjacent to the selected tooth. The differential distance for the selected tooth is the difference between these two distances. In one implementation, differential distances are determined in the plane of the archform. In this implementation, the minimum distance between a selected tooth and an adjacent tooth is used. In one implementation, the distances, and the differential distance, are vectors.

Figure 11:
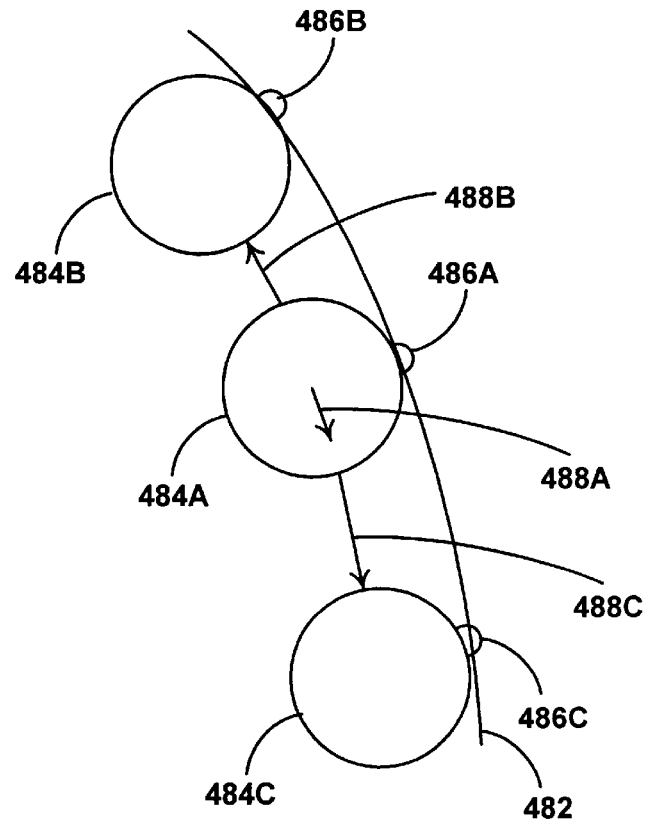
FIG. 11 depicts three teeth placed so that an archform passes through labial attachment points of the teeth.

FIG. 11 depicts three teeth 484A, B, and C, placed so that an archform 482 passes through respective labial attachment points 486A, B, and C. The distance between teeth 484A and 484B is represented by vector 488B. The distance between teeth 484A and 484C is represented by vector 488C. The differential distance for tooth 484A is represented by 488A, and is equal to the difference between vectors 488A and 488B.

Figure 12:
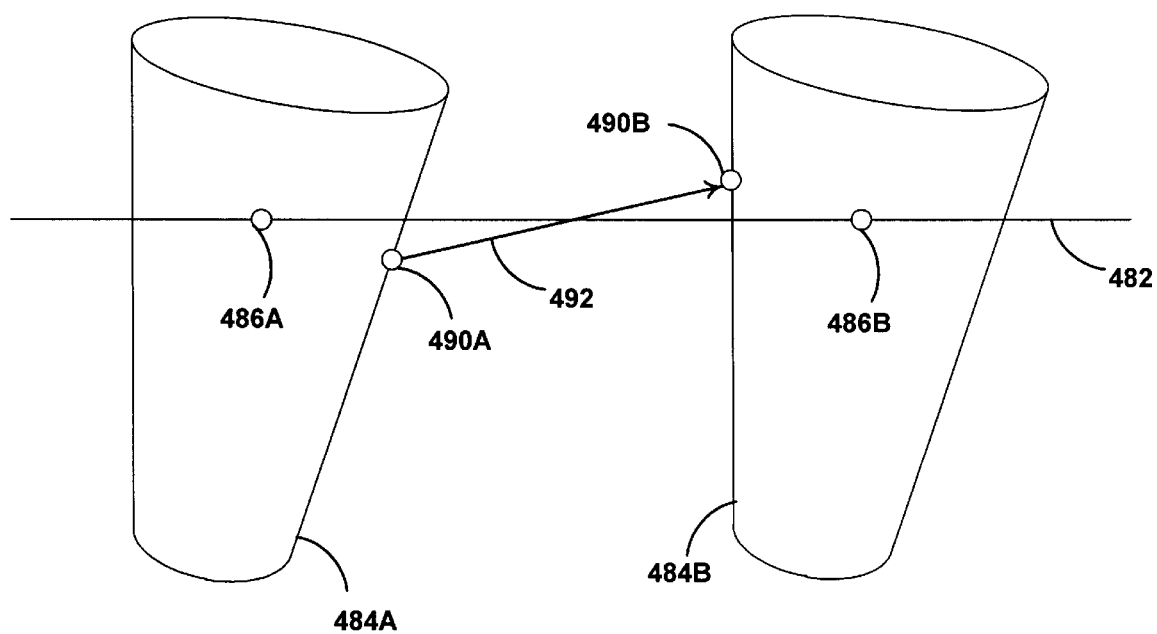
FIG. 12 depicts two teeth having respective attachment points on an archform.

FIG. 12 depicts two teeth 486A, and B having respective attachment points 486A, and B on archform 482. Each tooth has a measurement point. The process defines distal and mesial measurement points for each tooth. Referring to FIG. 11, a mesial measurement point 490A is defined for tooth 484A, and a distal measurement point 490B is defined for tooth 484B. Distances between teeth are measured between measurement points. For example, distance vector 492 is defined from measurement point 490A to measurement point 490B. For each tooth, a differential distance vector is calculated by taking the difference between the distance vectors for the tooth. Each tooth is moved according to its differential distance vector. In one implementation, the three-dimensional differential distance vector for a tooth is projected upon a tangent to the archform at the attachment point of the tooth to obtain a movement vector. The tooth is then moved according to the movement vector.

Figure 13:
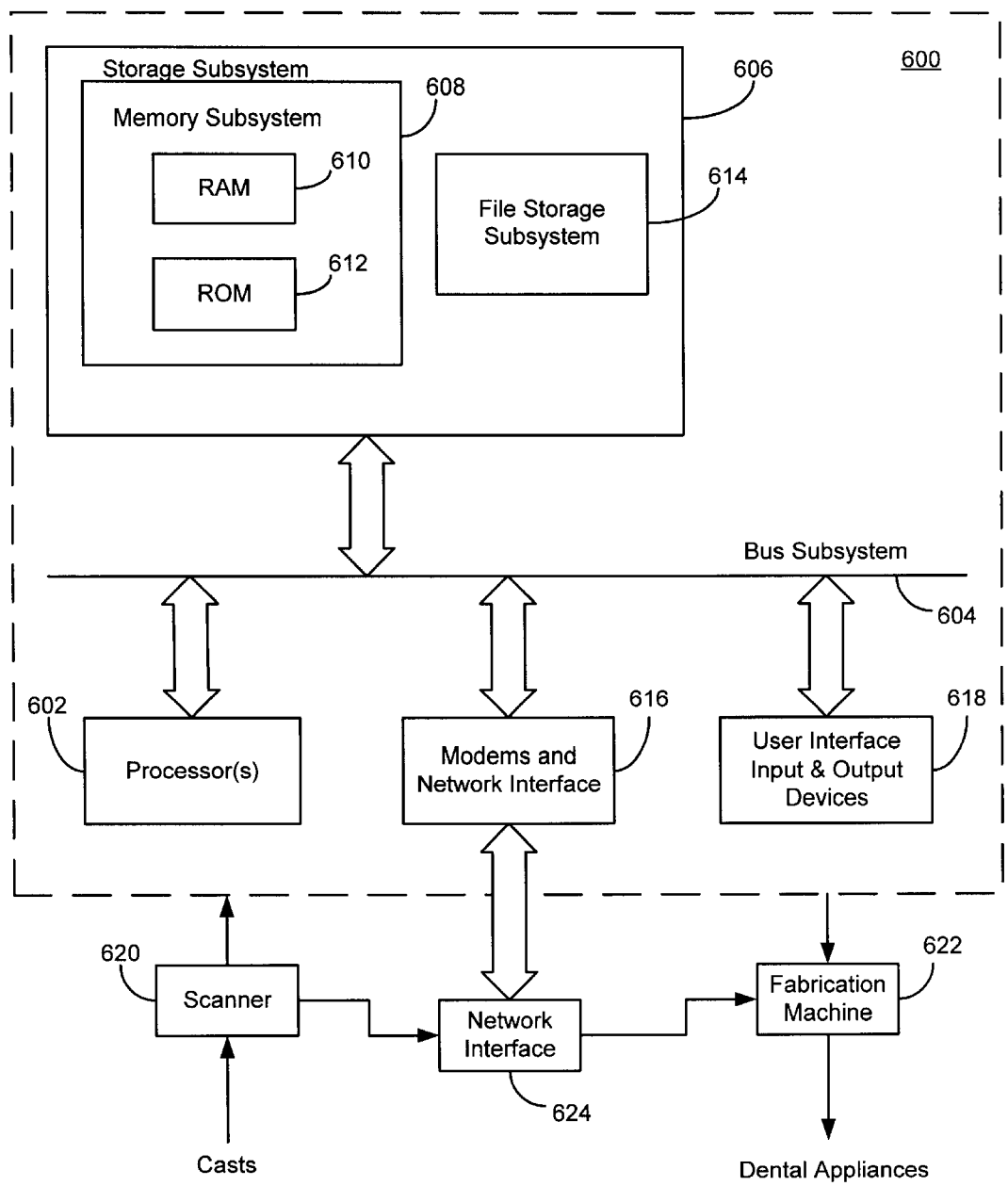
FIG. 13 is a block diagram illustrating a system for generating appliances in accordance with the present invention.

FIG. 13 is a simplified block diagram of a data processing system 500. Data processing system 500 typically includes at least one processor 502 that communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe. The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used. User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output. Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514. Memory subsystem 508 typically includes a number of memories including a main random access memory (RAM) 510 for storage of instructions and data during program execution and a read only memory (ROM) 512 in which fixed instructions are stored.

In the case of Macintosh-compatible personal computers the ROM would include portions of the operating system; in the case of IBM-compatible personal computers, this would include the BIOS (basic input/output system). File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations. Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system. Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524. Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription. Additionally, the techniques described here may be implemented in hardware or software, or a combination of the two. The techniques may be implemented in computer programs executing on programmable computers that each includes a processor, a storage medium readable by the processor □ (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A computer-implemented method for producing appliances to treat teeth, comprising:
   specifying a sequence of tooth movements to move the teeth through a series of discrete tooth arrangements, wherein at least some of the tooth arrangements are represented by digital data sets, wherein specifying a sequence of tooth movements comprises moving teeth according to an optimization function; and
   producing one or more appliances in accordance with the digital data sets wherein the appliances comprise polymeric shells having cavities and wherein the cavities of successive shells have different geometries shaped to receive and resiliently reposition teeth from one tooth arrangement to a successive tooth arrangement.

2. The computer-implemented method of claim 1, wherein the optimization function comprises moving teeth using force directed placement.

3. The computer-implemented method of claim 1, wherein the optimization function comprises moving teeth using simulated annealing.

4. The computer-implemented method of claim 1, wherein the optimization function comprises moving teeth using genetic algorithm.

5. The computer-implemented method of claim 1, wherein the optimization function comprises moving teeth by minimizing a cost function.

6. The computer-implemented method of claim 1, wherein specifying a sequence of tooth movements further comprises moving teeth using a random walk algorithm.

7. The computer-implemented method of claim 1, wherein specifying a sequence of tooth movements comprises moving teeth until the sum of differential distances for the plurality of teeth exceeds a predetermined threshold, thereby producing a final digital data set.

8. The computer-implemented method of claim 1, wherein specifying a sequence of tooth movements comprises:
   determining a first distance between a selected tooth and a first tooth that is adjacent to the selected tooth;
   determining a second distance between the selected tooth and a second tooth that is adjacent to the selected tooth; and
   calculating a difference between the first and second distances.

9. The computer-implemented method of claim 8, wherein the first and second distances are the minimum distances between the teeth.

10. The computer-implemented method of claim 1, further comprising:
    generating an initial final digital data set based on a masticatory system of a patient;
    generating at least one intermediate digital data set based on the initial digital data set and the final digital data set; and
    producing an incremental adjustment appliance based on each intermediate digital data set.

11. The method of claim 1, wherein specifying the sequence of tooth movements comprises:
    generating an initial digital data set representing an initial tooth arrangement;
    based on the initial digital data set, generating a second data set representing a second tooth arrangement; and,
    based on the second data set, generating a third data set representing a third tooth arrangement.

12. A computer-implemented method for producing appliances to treat teeth, comprising:
    specifying a sequence of tooth movements to move the teeth through a series of discrete tooth arrangements, wherein at least some of the tooth arrangements are represented by digital data sets,
    generating subsequent digital data sets based on prior digital data sets until a final digital data set representing an acceptable tooth arrangement is achieved; and
    producing one or more appliances in accordance with the digital data sets wherein the appliances comprise polymeric shells having cavities and wherein the cavities of successive shells have different geometries shaped to receive and resiliently reposition teeth from one tooth arrangement to a successive tooth arrangement.

13. An apparatus for producing appliances to treat teeth, the apparatus comprising:
    means for generating a digital arrangement of teeth;
    means for specifying a sequence of tooth movements to move the teeth to a target arrangement according to an optimization function; and
    means for generating one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

14. A computer program product, tangibly stored on a computer-readable medium, for producing appliances to treat teeth, comprising instructions operable to cause a programmable processor to:

generate a digital arrangement of teeth;

specify a sequence of tooth movements to move the teeth to a target arrangement according to an optimization function; and generate one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

15. A system for treating teeth, comprising:

a processor;

a display device coupled to the processor; and a data storage device coupled to the processor, the data storage device storing instructions operable to cause the processor to:

generate a digital arrangement of teeth;

specify a sequence of tooth movements to move the teeth to a target arrangement according to an optimization function; and generate one or more appliances in accordance with the specified sequence of tooth movements, the appliances comprise polymeric shells having cavities and wherein the cavities of successive shells have different geometries shaped to receive and resiliently reposition teeth from one arrangement to a successive arrangement.

16. The system of claim 15, wherein the specify instruction further comprises instructions to generate subsequent digital data sets based on prior digital data sets until a final digital data set representing an acceptable tooth arrangement is achieved.

17. The system of claim 15, wherein specify instructions comprises instructions to:

generate an initial digital data set representing an initial tooth arrangement;

based on the initial digital data set, generate a second data set representing a second tooth arrangement; and, based on the second data set, generate a third data set representing a third tooth arrangement.

18. The computer-implemented method of claim 15, wherein the optimization function comprises moving teeth using force directed placement, simulated annealing, genetic algorithm, cost minimization, or random walk algorithm.

* * * * *